United States Patent
Watsky

(10) Patent No.: US 6,245,766 B1
(45) Date of Patent: Jun. 12, 2001

(54) METHOD OF TREATING PSYCHIATRIC CONDITIONS

(75) Inventor: Eric J. Watsky, Stonington, CT (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 09/216,334

(22) Filed: Dec. 18, 1998

Related U.S. Application Data

(60) Provisional application No. 60/068,069, filed on Dec. 18, 1997.

(51) Int. Cl.$^7$ .................................................. A61K 31/495
(52) U.S. Cl. ...................................... 514/253.03; 544/368
(58) Field of Search ......................... 514/253.03

(56) References Cited

U.S. PATENT DOCUMENTS

| | | | |
|---|---|---|---|
| 4,831,031 | * 5/1989 | Lowe et al. | 514/254 |
| 4,883,795 | * 11/1989 | Lowe et al. | 514/253 |
| 5,206,366 | * 4/1993 | Bowles | 544/368 |
| 5,312,925 | * 5/1994 | Allen et al. | 544/368 |
| 5,338,846 | * 8/1994 | Busch et al. | 544/368 |
| 5,359,068 | * 10/1994 | Vrban | 544/368 |
| 5,935,960 | * 10/1999 | Waunsky et al. | 514/253 |

FOREIGN PATENT DOCUMENTS

| | | | |
|---|---|---|---|
| 2204451 | * 3/1998 | (CA) | . |
| 790236 | * 8/1997 | (EP) | . |
| 901786 | * 3/1999 | (EP) | . |
| 901789 | * 3/1999 | (EP) | . |
| 97 41896 | * 11/1997 | (WO) | . |
| 97 42190 | * 11/1997 | (WO) | . |
| 97 42191 | * 11/1997 | (WO) | . |

OTHER PUBLICATIONS

Davis, R., et al., *CNS Drugs* 1997, 9(2), 153–159.
Howard, H. R., et al., *J. Med. Chem.* 1996, 39(1), 143–148.
Lowe, J. A., et al., *J. Med. Chem.* 1991, 34(6), 1860–1866.
Seeger, T. F., et al., *The Journal of Pharmacology and Experimental Therapeutics* 1995, vol. 275, 101–113.
Wilner, K. D., et al., *Clinical Pharmacology & Therapeutics* 1996 (abstract).
Dorland's Illustrated Medical Dictionary, entry for "neuroleptic" (1994).
Stedman's Medical Dictionary (1995), entry for "neuroleptic".

* cited by examiner

*Primary Examiner*—Shep K. Rose
(74) *Attorney, Agent, or Firm*—Peter C. Richardson; Paul H. Ginsburg; A. David Joran

(57) ABSTRACT

A method for treating a psychiatic condition or disorder selected from anxiety disorders such as panic disorder, posttraumatic stress disorder and phobias, psychotic episodes of anxiety, anxiety associated with psychosis, psychotic mood disorders such as severe major depressive disorder and mood disorders associated with psychotic disorders such as acute mania or depression associated with bipolar disorder, schizophrenia, behavioral manifestations of mental retardation, conduct disorder or autistic disorder, dementias such as dementias of the Alzheimer's type, and dyskinesias such as drug induced and neurodegeneration based dyskinesias in a mammal, including a human, comprising administering to said mammal a pharmaceutically effective amount of a compound of the formula (I)

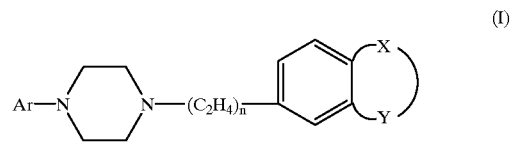

or a pharmaceutically acceptable acid addition salt thereof, wherein n, X, Y and Ar are as defined above.

17 Claims, No Drawings

METHOD OF TREATING PSYCHIATRIC CONDITIONS

This application claims the benefit of Provisional Ser. No. 60/068,069 filed Dec. 18, 1997.

BACKGROUND OF THE INVENTION

The present invention relates to the use of piperazinyl-heterocyclic compounds of the formula I, as defined below, for the treatment of certain psychiatric disorders and conditions that have as symptoms behavioral disturbances. Such psychiatric disorders and conditions include anxiety disorders such as generalized anxiety disorder, panic disorder, posttraumatic stress disorder and phobias; psychotic episodes of anxiety, anxiety associated with psychosis, psychotic mood disorders such as severe major depressive disorder; mood disorders associated with psychotic disorders such as acute mania and depression associated with bipolar disorder, mood disorders associated with schizophrenia; behavioral disturbances associated with mental retardation, autistic disorder, and conduct disorder; dementias such as dementias associated with Alzheimer's disease; and drug-induced and neurodegeneration based dyskinesias.

The piperazinyl-heterocyclic compounds of formula I of this invention, useful in the treatment of psychotic disorders, are referred to in U.S. Pat. Nos. 4,831,031 and 4,883,795, both of which are assigned in common with the present application.

SUMMARY OF THE INVENTION

The present invention relates to a method for treating a psychiatric condition or disorder selected from anxiety disorders such as generalized anxiety disorder, panic disorder, posttraumatic stress disorder and phobias; psychotic episodes of anxiety, anxiety associated with psychosis, psychotic mood disorders such as severe major depressive disorder; mood disorders associated with psychotic disorders such as acute mania or depression associated with bipolar disorder and mood disorders associated with schizophrenia, behavioral manifestations of mental retardation, conduct disorder and autistic disorder; dementias such as dementias of the Alzheimer's type; and dyskinesias such as drug induced and neurodegeneration based dyskinesias in a mammal, including a human, comprising administering to said mammal a pharmaceutically effective amount of a compound of the formula

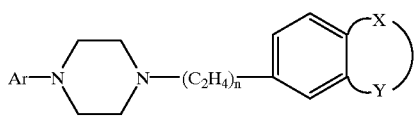

(I)

or a pharmaceutically acceptable acid addition salt thereof, wherein

Ar is benzoisothiazolyl or an oxide or dioxide thereof each optionally substituted by one fluoro, chloro, trifluoromethyl, methoxy, cyano, nitro or naphthyl optionally substituted by fluoro, chloro, trifluoromethyl, methoxy, cyano or nitro; quinolyl; 6-hydroxy-8-quinolyl; isoquinolyl; quinazolyl; benzothiazolyl; benzothiadiazolyl; benzotriazolyl; benzoxazolyl; benzoxazolonyl; indolyl; indanyl optionally substituted by one or two fluoro, 3-indazolyl optionally substituted by 1-trifluoromethylphenyl; or phthalazinyl;

n is 1 or 2; and

X and Y together with the phenyl to which they are attached form quinolyl; 2-hydroxyquinolyl; benzothiazolyl; 2-aminobenzothiazolyl; benzoisothiazolyl; indazolyl; 2-hydroxyindazolyl; indolyl; spiro; oxindolyl optionally substituted by one to three of $(C_1-C_3)$alkyl, or one of chloro, fluoro or phenyl, said phenyl optionally substituted by one chloro or fluoro; benzoxazolyl; 2-aminobenzoxazolyl; benzoxazolonyl; 2-aminobenzoxazolinyl; benzothiazolonyl; bezoimidazolonyl; or benzotriazolyl. The foregoing method is referred to hereinafter as the "inventive method".

The term "treating", as used herein, refers to reversing, alleviating, inhibiting the progress of, or preventing the disorder or condition to which such term applies, or one or more symptoms of such disorders or condition. The term "treatment", as used herein, refers to the act of treating, as "treating" is defined immediately above.

The term "pharmaceutically effective amount", as used herein, refers to an amount of the compound of formula I sufficient to treat a psychiatric condition or disorder selected from anxiety disorders such as generalized anxiety disorder, panic disorder, posttraumatic stress disorder and phobias; psychotic episodes of anxiety, anxiety associated with psychosis; psychotic mood disorders such as severe major depressive disorder; mood disorders associated with psychotic disorders such as acute mania or depression associated with bipolar disorder; mood disorders associated with schizophrenia; behavioral manifestations of mental retardation, conduct disorder and autistic disorder; dementias such as dementias of the Alzheimer's type; and dyskinesias such as drug induced and neurodegeneration based dyskinesias in a mammal, including a human.

A preferred embodiment of this invention relates to the above inventive method wherein the compound administered is used for treating dementia.

Another preferred embodiment of this invention relates to the above inventive method wherein dementia that is treated is selected from the group consisting of vascular dementia, dementia due to HIV disease, dementia due to head trauma, dementia due to Parkinson's disease, dementia due to Huntington's disease, dementia due to Pick's disease, dementia due to Creutzfeldt-Jakob disease, substance-induced persisting dementia, dementia due to multiple etiologies and dementia not otherwise specified (NOS).

Another preferred embodiment of this invention relates to the above inventive method wherein the compound administered is used for treating dementia of the Alzheimer's type.

Another preferred embodiment of this invention relates to the above inventive method wherein the dementia that is treated is dementia of the Alzheimer's type and is selected from the group consisting of dementia of the Alzheimer's type with early onset uncomplicated, dementia of the Alzheimer's type with early onset with delusions, dementia of the Alzheimer's type with early onset with depressed mood, dementia of the Alzheimer's type with late onset uncomplicated, dementia of the Alzheimer's type with late onset with delusions and dementia of the Alzheimer's type with late onset with depressed mood.

Another preferred embodiment of this invention relates to the above inventive method wherein the compound administered is used for treating generalized anxiety disorder.

Another preferred embodiment of this invention relates to the above inventive method wherein the anxiety disorder is selected from the group consisting of panic disorder without agoraphobia, panic disorder with agoraphobia, agoraphobia without history of panic disorder, social phobia, postraumatic stress disorder, acute stress disorder, generalized anxiety disorder, substance-induced anxiety disorder and anxiety disorder not otherwise specified (NOS).

Another preferred embodiment of this invention relates to the above inventive method wherein the compound administered is used for treating a psychotic mood disorder.

Another preferred embodiment of this invention relates to the above inventive method wherein psychotic mood disorder is selected from the group consisting of depressive disorders, bipolar disorders, mood disorder with depressive features, mood disorder with major depressive-like episode, mood disorder with manic features, mood disorder with mixed features, substance-induced mood disorder and mood disorder not otherwise specified (NOS).

Another preferred embodiment of this invention relates to the above inventive method wherein depressive disorders are selected from major depressive disorder (single episode) and major depressive disorder (recurrent).

Another preferred embodiment of this invention relates to the above inventive method wherein the current state of major depressive disorder (single episode) and major depressive disorder (recurrent) are each characterized as mild, moderate, severe without psychotic features, severe with psychotic features, in partial remission or in full remission.

Another preferred embodiment of this invention relates to the above inventive method wherein bipolar disorders are selected from the group consisting of bipolar I or II disorder (single manic episode), bipolar I or II disorder (most recent episode hypomanic), bipolar I or II disorder (most recent episode manic, bipolar I or II disorder most recent episode mixed, bipolar I or II disorder most recent episode depressed), cyclothymic disorder and bipolar disorder not otherwise specified (NOS).

Another preferred embodiment of this invention relates to the above inventive method wherein the current state of bipolar I or II disorder (single manic episode), bipolar I or It disorder (most recent episode manic), bipolar I or II disorder (most recent episode depressed) are each characterized as mild, moderate, severe without psychotic feactures, severe with psychotic features, in partial remission or in full remission.

Another preferred embodiment of this invention relates to the above inventive method wherein the compound administered is used for treating schizophrenia.

Another preferred embodiment of this invention relates to the above inventive method wherein schizophrenia is selected from the group consisting of paranoid type, disorganized type, catatonic type, undifferentiated type and residual type.

Another preferred embodiment of this invention relates to the above inventive method wherein the compound administered is used for treating dyskinesias.

Another preferred embodiment of this invention relates to the above inventive method wherein dyskinesias is selected from drug-induced dyskinesias and neurodegenerative based dyskinesias.

Another preferred embodiment of this invention relates to the above inventive method wherein the compound administered is used for treating behavioral manifestations of mental retardation.

Another preferred embodiment of this invention relates to the above inventive method wherein mental retardation is selected from the group consisting of mild mental retardation, moderate mental retardation, severe mental retardation, profound mental retardation and mental retardation severity unspecified.

Another preferred embodiment of this invention relates to the above inventive method wherein the compound administered is used for treating behavioral manifestations of conduct disorder.

Another preferred embodiment of this invention relates to the above inventive method wherein the compound administered is used for treating behavioral manifestations of autistic disorder.

Another preferred embodiment of this invention relates to the above inventive method or any of the above specified variations of such method wherein the compound administered is one wherein Ar is benzoisothiazolyl and n is 1.

Another preferred embodiment of this invention relates to the above inventive method or any of the above specified variations of such method wherein the compound administered is one wherein X and Y, together with the phenyl to which they are attached, form oxindole optionally substituted by chloro, fluoro or phenyl.

Another preferred embodiment of this invention relates to the above inventive method or any of the above specified variations of such method wherein the compound administered is one wherein Ar is naphthyl and n is 1.

All the psychiatric disorders and conditions referred to herein are known to those of skill in the art and defined as in the Diagnostic and Statistical Manual of Mental Disorders, Fourth Edition, American Psychiatric Association, 1994 (DMS IV), which is incorporated herein by reference in its entirety.

DETAILED DESCRIPTION OF THE INVENTION

The piperazinyl-heterocyclic compounds of formula I can be prepared by one or more of the synthetic methods described and referred to in U.S. Pat. Nos. 4,831,031 and 4,883,795. U.S. Pat. Nos. 4,831,031 and 4,883,795 are incorporated herein by reference in their entirety.

The compounds of formula I may be prepared by reacting piperazines of formula II with compounds of formula III as follows:

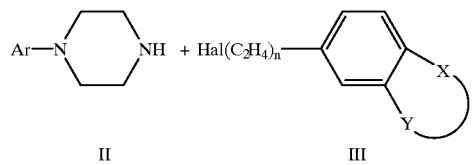

II          III wherein Hal is fluoro, chloro, bromo or iodo. This coupling reaction is generally conducted in a polar solvent such as a lower alcohol, for instance ethanol, dimethylformamide or methylisobutylketone, and in the presence of a weak base such as a tertiary amine base, for instance triethylamine or diisopropylethylamine. Preferably, the reaction is in the further presence of a catalytic amount of sodium iodide, and a neutralizing agent for hydrochloride such as sodium carbonate. The reaction is preferably conducted at the reflux temperature of the solvent used. The piperazine derivatives of formula II may be prepared by methods known in the art. For instance, preparation may be by reacting an arylhalide of the formula ArHal wherein Ar is as defined above and Hal is fluoro, chloro, bromo or iodo, with piperazine in a hydrocarbon solvent such as toluene at about room temperature to reflux temperature for about half an hour to 24 hours. Alternatively, the compounds of formula II may be prepared by heating an amino-substituted aryl compound of the formula $ArNH_2$ wherein Ar is as defined above with a secondary amine to allow cyclization to form the piperazine ring attached to the aryl group Ar.

The compounds of formula III may be prepared by known methods. For instance, compounds (III) may be prepared by reacting a halo-acetic acid or halo-butyric acid wherein the halogen substituted is fluoro, chloro, bromo or iodo with a compound of the formula IV as follows:

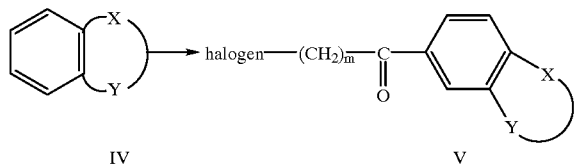

wherein X and Y are as defined above and m is 1 or 3. The compounds (V) are then reduced, e.g. with triethylsilane and trifluoroacetic acid in a nitrogen atmosphere, to form compounds (III).

When Ar is the oxide or dioxide of benzoisothiazolyl, the corresponding benzoisothiazolyl is oxidized under acid conditions at low temperatures. The acid used is advantageously a mixture of sulphuric acid and nitric acid.

The pharmaceutically acceptable acid addition salts of the compounds of formula I are prepared in a conventional manner by treating a solution or suspension of the free base (I) with about one chemical equivalent of a pharmaceutically acceptable acid. Conventional concentration and recrystallization techniques are employed in isolating the salts. Illustrative of suitable acids are acetic, lactic, succinic, maleic, tartaric, citric, gluconic, ascorbic, benzoic, cinnamic, fumaric, sulfuric, phosphoric, hydrochloric, hydrobromic, hydroiodic, sulfamic, sulfonic such as methanesulfonic, benzenesulfonic, and related acids.

Compounds of formula I, and their pharmaceutically acceptable salt (referred to collectively hereinafter, as "the active compounds of this invention"), can be administered to a human subject either alone, or, preferably, in combination with pharmaceutically-acceptable carriers or diluents, in a pharmaceutical practice. Such compounds can be administered orally or parenterally. Parenteral administration includes especially intravenous and intramuscular administration. Additionally, in a pharmaceutical composition comprising an active compound of this invention, the weight ratio of active ingredient to carrier will normally be in the range from 1:6 to 2:1, and preferably 1:4 to 1:1. However, in any given case, the ratio chosen will depend on such factors as the solubility of the active component, the dosage contemplated and the precise route of administration.

For oral use in treating psychiatric conditions whose manisfestations include psychiatric symptoms or behavioral disturbance, the active compounds of this invention can be administered, for example, in the form of tablets or capsules, or as an aqueous solution or suspension. In the case of tablets for oral use, carriers which can be used include lactose and corn starch, and lubricating agents, such as magnesium stearate, can be added. For oral administration in capsule form, useful diluents are lactose and dried corn starch. When aqueous suspensions are required for oral use, the active ingredient can be combined with emulsifying and suspending agents. If desired, certain sweetening and/or flavoring agents can be added. For intramuscular, parenteral and intravenous use, sterile solutions of the active ingredient can be prepared, and the pH of the solutions should be suitably adjusted and buffered. For intravenous use, the total concentration of solutes should be controlled to render the preparation isotonic.

When an active compound of this invention is to be used in a human subject to treat psychiatric conditions whose manisfestations include psychiatric symptoms or behavioral disturbance, the daily dosage will normally be determined by the prescribing physician. Moreover, the dosage will vary according to the age, weight and response of the individual patient as well as the severity of the patient's symptoms. However, in most instances, an effective amount for treating psychiatric conditions whose manisfestations include psychiatric symptoms or behavioral disturbance, will be a daily dosage in the range from 0.5 to 500 mg, and preferably 10 mg a day to 80 mg a day, in single or divided doses, orally or parenterally. In some instances it may be necessary to use dosages outside these limits.

The receptor binding and neurotransmitter uptake inhibition profile for ziprasidone, 5-(2-(4-(1,2-benzisothiazol-3-yl)piperazinyl)ethyl)chlorooxindole hydrochloride, was described in The Journal of Pharmacology and Experimental Therapeutics, 275, 101–113 (1995), which is incorporated herein by reference in its entirety. A summary of its affinity for various receptors in the central nervous system tissue is presented in Table 1.

TABLE 1

|  | Ziprasidone |
| --- | --- |
| Receptor (Ligand) |  |
| DA D1([$^3$H]SCH23390) | 6.28 + 0.17 (3) |
| DA D2([$^3$H]spiperone) | 8.32 + 0.04 (6) |
| DA D3([$^3$H]raclopride) | 8.14 + 0.03 (3) |
| DA D4[$^3$H]spiperone) | 7.49 + 0.11 (3) |
| 5-HT2A([$^3$H]ketanserin) | 9.38 + 0.03 (5) |
| 5-HT1A([$^3$H]-80H-DPAT) | 8.47 + 0.05 (4) |
| 5-HT2C- ([$^3$H]mesulergine) | 8.88 + 0.05 (6) |
| 5-HT1D- ([$^3$H]-5-HT) | 8.69 + 0.04 (6) |
| Alpha-1 ([$^3$H]prazosin) | 7.98 + 0.03 (3) |
| Histamine H1 ([$^3$H]mepyramine) | 7.33 + 0.07 (3) |
| Neurotransmitter Reuotake Biockade: |  |
| Norpinephrine | 7.30 + 0.01 (4) |
| 5-HT | 7.29 + 0.06 (3) |
| DA | 6.58 + 0.02 (3) |

Ziprasidone has been found effective for the following indications: psychotic disorders, acute mania, anxiety states, schizophrenia, bipolar disorder, Alzheimer's disease (delusions, delirium), depression and psychotic disorders.

The following examples illustrate methods of preparing various compounds of formula I.

EXAMPLE 1

6-(2-(4-(1-Naphthyl)piperazinyl)ethyl)-benzoxazolone

A. To a 500 ml three-necked round-bottomed flask equipped with mechanical stirrer and nitrogen inlet were added 200 grams of polyphosphoric acid, 13.51 grams (0.1 mole) of benzoxazolone, and 13.89 g (0.1 mole) of bromoacetic acid. The reaction was heated with stirring at 115° C. for 2.5 hours and poured into 1 kg ice. The mixture was stirred mechanically for 1 hour to form a purple solid, which was then filtered off and washed with water. The solid was slurried with acetone for 30 minutes, a small amount of purple solid filtered off, and the brown filtrate evaporated. The resulting dark brown gum was slurried with 150 ml ethanol for 30 minutes, and the brown solid filtered off and washed with ethanol. This solid had a m.p. of 192°–194° C.

The solid (6.6 grams, 0.0257 mole) was placed in a 100 ml three-necked round-bottomed flask equipped with magnetic stirrer, dropping funnel, thermometer, and nitrogen inlet and 19.15 ml (0.257 mole) of trifluoroacetic acid added. Triethylsilane (9.44 ml, 0.0591 mole) was added dropwise to the stirring slurry over 30 minutes. The reaction was stirred overnight at room temperature, then poured into 150 grams ice. The mixture was stirred for 15 minutes, and the brown gum filtered off. The gum was dissolved in 100 ml ethyl acetate, and 125 ml cyclohexane added, giving a brown precipitate, which was filtered and washed with cyclohexane. The filtrate was evaporated and the resulting yellow solid slurried with 50 ml isopropyl ether the pale yellow solid was filtered off and dried to give 2.7 g 6-(2-bromoethyl)-benzoxazolone (11% yield for two steps), m.p. 148°–151° C.

B. To a 100 ml round-bottomed flask equipped with magnetic stirrer, condenser, and nitrogen inlet were added 0.618 g (2.10 mmol) of N-(1-naphthyl)piperazine 0.472 g (1.95 mmol) of 6-(2-bromoethyl)-benzoxazolone, 0.411 ml (2.92 mmol) of triethylamine, 50 ml ethanol, and a catalytic amount of sodium iodide. The reaction was refluxed for 3 days, cooled, and evaporated to a brown gum. The gum was partitioned between 50 ml water and 75 ml methylene chloride, the pH adjusted with aqueous 1 N sodium hydroxide solution, and a little methanol added to facilitate phase separation. The methylene chloride layer was dried over sodium sulfate and evaporated, then chromatographed on silica gel. Fractions containing the product were combined and evaporated, the residue taken up in ethyl acetate, treated with hydrochloride gas, and the resulting hydrochloride salt of the product filtered off to give the while solid title compound, m.p. 282°–285° C., 213 mg (23% yield).

EXAMPLE 2

6-(2-(4-(1-Naphthyl)piperazinyl)ethyl)-benzimidazolone

A. To a 500 ml three-necked round-bottomed flask equipped with mechanical stirrer and nitrogen inlet were added 100 grams of polyphosphoric acid, 6.7 grams (0.05 mole) of benzoxazolone, and 6.95 grams (0.05 mole) of bromoacetic acid. The reaction was heated with stirring at 115° C. for 1.5 hours and poured into 1 kg ice. The mixture was stirred mechanically for 1 hour to form a gray solid, which was then filtered off and washed with water. The solid was slurried with acetone for 30 minutes, a small amount of purple solid filtered off, and the brown filtrate evaporated. The resulting dark brown gum was taken up in ethyl acetate/water, and the organic layer washed with water and brine, dried, and evaporated to solid, 6.5 grams (51%). NMR (d, DMSO-$d_6$): 5.05 (s, 2H), 7.4 (m, 1H), 7.7–8.05 (m, 2H).

The solid (6.0 grams, 0.0235 mole) was placed in a 100 ml three-necked round-bottomed flask equipped with magnetic stirrer, dropping funnel, thermometer, and nitrogen inlet and 18.2 ml (0.235 mole) of trifluoroacetic acid added. Triethylsilane (8.64 ml, 0.0541 mole) was added dropwise to the stirring slurry over 30 minutes. The reaction was stirred overnight at room a temperature, then poured into 150 grams ice. The mixture was stirred for 14 minutes, and the pink solid 6-(2-bromoethyl)-benzimidazolone filtered off to give 5.0 grams (42% yield for two steps), m.p. 226°–220° C.

B. To a 100 ml round-bottomed flask equipped with magnetic stirrer, condenser, and nitrogen inlet were added 2.64 grams (12.4 mmol) of N-(1-naphthyl)-piperazine, 3.0 grams (12.4 mmol) of 6-(2-bromoethyl)-benzimidazolone, 1.31 grams (12.4 mmol) sodium carbonate, 50 ml methylisobutylketone, and a catalytic amount of sodium iodide. The reaction was refluxed for 3 days, cooled, and evaporated to a brown gum. The gum was partitioned between 50 ml water and 75 ml ethyl acetate, and the ethyl acetate layer washed with brine, dried over sodium sulfate, and evaporated, then chromatographed on silica gel. Fractions containing the product were combined and evaporated, the residue taken up in tetrahydrofuran, treated with hydrochloric acid gas, and the resulting hydrochloride salt of the product filtered off to give a white solid, m.p. 260°–262° C., 716 mg (14% yield).

EXAMPLE 3

6-(2-(4-(8-Quinolyl)piperazinyl)ethyl)-benzoxazolone

To a 35 ml round-bottomed flask equipped with condenser and nitrogen inlet were added 0.36 grams (1.5 mmol) of 6-bromoethyl benzoxazolone, 0.32 grams (1.5 mmol) of 8-piperazinyl quinoline, 0.2 grams (1.9 mmol) of sodium carbonate, 50 mg of sodium iodide, and 5 ml of ethanol. The reaction was refluxed for 20 hours, cooled, diluted with water, and the pH adjusted to 4 with 1 N Sodium hydroxide, and the product extracted into ethyl acetate. The ethyl acetate layer was washed with brine, dried, and evaporated to give 0.3 grams of a yellow oil. The oil was dissolved in ethyl acetate, ethyl acetate saturated with hydrochloric acid gas added, and the mixture concentrated to dryness. The residue was crystallized from isopropanol to give 0.18 grams (32%) of a yellow salt, m.p. 200° NMR (d, CDCl$_3$): 2.74 (m, 2H), 2.89 (m, 6H), 3.44 (m, 4H), 6.76–7.42 (m, 7H), 8.07 (m, 1H), 8.83 (m, 1H).

EXAMPLE 4

6-(2-(4-(6-Quinolyl)piperazinyl)ethyl)-benzoxazolone

To a 35 ml round-bottomed flask equipped with condenser and nitrogen inlet were added 0.36 grams (1.5 mmol) of 6bromoethylbenzoxazolone, 0.32 g (1.5 mmol) of 8-piperazinylquinazoline, 0.85 grams (8.0 mmol) of sodium carbonate, 2 mg of sodium iodide, and 35 ml of ethanol. The reaction was refluxed for 3 days, cooled, diluted with water, and the pH adjusted to 4 with 1 N HCl. The aqueous layer was separated, the pH adjusted to 7 with 1 N Sodium hydroxide, and the product extracted into ethyl acetate. The ethyl acetate layer was washed with brine, dried, and evaporated to give 1.3 grams of a yellow oil. The oil was crystallized form chloroform (1.1 g), dissolved in ethyl acetate, ethyl acetate saturated with hydrochloric acid gas added, and the mixture concentrated to dryness. The residue gave 0.9 grams (58%) of a yellow salt, m.p. 200° C. NMR (d, CDCl$_3$): 2.72 (m, 6H), 2.86 (m, 2H), 3.83 (m, 4H), 6.9–7.9 (m, 7H), 8.72 (s, 1H).

EXAMPLE 5

6-(2-(4-(4-Phthalazinyl)piperazinyl)ethyl)-benzoxazolone

To a 35 ml round-bottomed flask equipped with condenser and nitrogen inlet were added 1.13 grams (4.7 mmol) of 6-bromoethyl benzoxazolone, 1.0 gram (4.7 mmol) of 4-piperazinyl phthalazine, 0.64 grams (6.0 mmol) of sodium carbonate, and 30 ml of ethanol. The reaction was refluxed for 20 hours, cooled, diluted with water, and the pH adjusted to 4 with 1 N HCl. The aqueous layer was separated, the pH adjusted to 7 with 1 N Sodium hydroxide, and the product extracted into ethyl acetate. The ethyl acetate layer was washed with brine, dried, and evaporated to give 0.5 grams of a red oil. The oil was chromatographed on silica gel using chloroform/methanol as eluent to give 0.2 grams of a pink oil. The oil was dissolved in ethyl acetate, ethyl acetate saturated with hydrochloric acid gas added and the mixture concentrated to give 0.37 grams (11%) of a yellow salt, m.p. 200° C. NMR (d, CDCl$_3$): 2.78 (m, 2H), 2.88 (m, 6H), 3.65 (m, 4H), 7.0–8.1 (m, 7H), 9.18 (s, 1H).

EXAMPLE 6

6-(2-(4-(4-Methoxy-1-naphthyl)piperazinyl)ethyl)-benzoxazolone

To a 35 ml round-bottomed flask equipped with condenser and nitrogen inlet were added 0.24 grams (1.0 mmol) of 6-bromoethylbenzoxazolone, 0.24 grams (1.0 mmol) of 4-methoxy-1-piperazinylnaphthalene, 0.13 grams (1.2 mmol) of sodium carbonate, and 25 ml of ethanol. The reaction was refluxed for 36 hours, cooled, diluted with water, and the product extracted into ethyl acetate. The ethyl acetate layer was washed with brine, dried, and evaporated to give 0.49 grams of a yellow oil. The oil was chromatographed on silica gel using chloroform as eluent to give 0.36 grams of yellow crystals. The solid was dissolved in ethyl acetate, ethyl acetate saturated with hydrochloric acid gas added, and the mixture concentrated to dryness to give 0.26 grams (55%) of white salt crystals, m.p. 200° C. NMR (d, CDCl$_3$): 2.8–3.2 (m, 12H), 4.01 (s, 3H), 6.7–7.6 (m, 7H), 8.26 (m, 2H).

EXAMPLE 7

6-(2-(4-(5-Tetralinyl)piperazinyl)ethyl)-benzoxazolone

To a 35 ml round-bottomed flask equipped with condenser and nitrogen inlet were added 1.0 gram (3.9 mmol) of 6-bromoethylbenzoxazolone, 0.85 grams (3.9 mmol) of 5-piperazinyltetralin, 0.4 grams (3.9 mmol) of sodium carbonate, 2 mg of sodium iodide, and 30 ml of isopropanol. The reaction was refluxed for 18 hours, cooled, evaporated to dryness, and the residue dissolved in ethyl acetate/water. The pH was adjusted to 2.0 with 1 N HCl, and the precipitate which had formed collected by filtration. The precipitate was suspended in ethyl acetate/water, the pH adjusted to 8.5 with 1 N Sodium hydroxide, and the ethyl acetate layer separated. The ethyl acetate layer was washed with brine, dried, and evaporated to give 0.7 grams of a solid. The solid was dissolved in ethyl acetate, ethyl acetate saturated with hydrochloric acid gas added, and the mixture concentrated to dryness to give 0.70 grams (40%) of a yellow salt, m.p. 200° C. NMR (d, CDCl$_3$): 1.9 (m, 4H), 2.95 (m, 16H), 6.8–7.2 (m, 6H).

EXAMPLE 8

6-(2-(4-(6-Hydroxy-8-quinolyl)piperazinyl)ethyl)-benzoxazolone

To a 35 ml round-bottomed flask equipped with condenser and nitrogen inlet were added 0.84 grams (3.5 mmol) of 6-bromoethylbenzoxazolone, 0.80 grams (3.5 mmol) of 6-hydroxy-8-piperazinyl quinoline, 0.37 grams (3.5 mmol) of sodium carbonate, 2 mg of sodium iodide, and 30 ml of isopropanol. The reaction was refluxed for 18 hours, cooled, evaporated, and the residue dissolved in ethyl acetate/water. The pH was adjusted to 2.0 with 1 N HCl, and the phases separated. The aqueous phase was adjusted to pH 8.5 and extracted with ethyl acetate. The ethyl acetate layer was washed with brine, dried, and evaporated to give 0.33 grams of a yellow solid. The solid was dissolved in ethyl acetate, ethyl acetate saturated with hydrochloric acid gas added, and the mixture concentrated to dryness. The residue was crystallized from isopropanol to give 0.32 grams (20%) of a yellow salt, m.p. 200° C. NMR (d, CDCl$_3$): 2.8 (m, 8H), 3.4 (m, 4H), 6.7–7.3 (m, 7H), 7.7–7.9 (m, 1 H).

EXAMPLE 9

6-(2-(4-(1-(6-Fluoro)naphthyl)piperazinyl)ethyl)-benzoxazolone

A. To a round-bottomed flask equipped with condenser and nitrogen inlet were added 345 ml (3.68 mol) of fluorebenzene and 48 grams (0.428 mol) of furoic acid. To the stirring suspension was added in portion 120 grams (0.899 mol) of aluminum chloride. The reaction was then stirred at 95° C. for 16 hours and then quenched by addition to ice/water/1 N HCl. After stirring 1 hour, the aqueous layer was decanted off, and benzene and a saturated aqueous solution of sodium bicarbonate added. After stirring 1 hour, the layers were separated, the aqueous layer washed with benzene, acidified, and extracted into ethyl acetate. The ethyl acetate layer was washed with water and brine, dried over sodium sulfate, and evaporated to a solid. The solid was triturated with isopropyl ether to give 5.0 grams (6.1%) of white solid 6-fluoro-1-naphthoic acid, NMR (d, DMSO-d$_6$): 7.0–8.0 (m, 5H), 8.6 (m, 1 H).

B. To a 125 ml round-bottomed flask equipped with condenser, addition funnel, and nitrogen inlet were added 5.0 grams (26.3 mmol) of 6-fluoro-1-naphthoic acid and 50 ml acetone. To the stirring suspension were added dropwise 6.25 ml (28.9 mmol) of diphenyl phosphoryl azide and 4 ml (28.9 mmol) of triethylamine. The reaction was refluxed 1 hour, poured into water/ethyl acetate, and filtered. The filtrate was washed with water and brine, dried over sodium sulfate, and evaporated. The residue was further treated with hydrochloric acid to form the hydrochloride salt and then liberated with sodium hydroxide to afford the free base 6-fluoro-1-amino-naphthalene as an oil, 1.0 gram (24%).

C. To a 125 ml round-bottomed flask equipped with condenser and nitrogen inlet were added 1.0 gram (6.21 mmol) of 6-fluoro-1-amino naphthalene, 1.8 grams (7.76 mmol) of N-benzyl bis(2-chloroethyl)amine hydrochloride, 3.3 ml (19.2 mmol) of diisopropylethylamine, and 50 ml isopropanol. The reaction was refluxed 24 hours, cooled, and evaporated to an oil. The oil was taken up in ethyl acetate, washed with water and brine, dried over sodium sulfate, and evaporated to an oil. The oil was chromatographed on silica gel using methylene chloride as eluent to afford 1.5 grams (75.5%) of an oil, 1-benzyl-4-(6-fluoronaphthyl)-piperazine.

D. To a 125 ml round-bottomed flask equipped with nitrogen inlet were added 1.5 grams (4.69 mmol) of 1-benzyl4-(6-fluoronaphthyl)-piperazine, 1.2 ml (31.3 mmol) of formic acid, 3.0 grams 5% palladium on carbon, 50 ml ethanol. The reaction was stirred at room temperature for 16 hours, the catalyst filtered under N$_2$, and the solvent evaporated. The oil, N-(1-(6-fluoro)naphthyl)-piperazine (0.420 grams, 39%), was used directly in the following step.

E. To a 100 ml round-bottomed flask equipped with magnetic stirrer, condenser, and nitrogen inlet were added 0.420 grams (1.83 mmol) of N-(1-naphthyl)piperazine, 0.440 grams (1.83 mmol) of 6-(2-bromoethyl)-benzoxazolone, 194 mg (1.83 mmol) of sodium carbonate, 50 ml methylisobutylketone, and a catalytic amount of sodium iodide. The reaction was refluxed for 3 days, cooled, and evaporated to a brown gum. The gum was partitioned between 50 ml water and 75 ml ethyl acetate, the pH adjusted with aqueous 1 N Sodium hydroxide solution, the layers separated, and the ethyl acetate layer washed with water and brine. The ethyl acetate layer was dried over sodium sulphate and evaporated, then chromatographed on silica gel. Fractions containing the product were combined and evaporated, the residue taken up in ether/methylene chloride, treated with hydrochloric acid gas, and the resulting hydrochloride salt of the product filtered off to give a white solid, m.p. 295°–300° C., 214 mg (22% yield).

EXAMPLE 10

6-(4-(4-(1-Naphthyl)piperazinyl)butyl)-benzoxazolone

A. To a 500 ml round-bottomed flask equipped with mechanical stirrer and nitrogen inlet were added 200 grams polyphosphoric acid, 16.7 grams (0.1 mol) 4-bromobutyric acid, and 13.51 grams (0.1 mol) benzoxazolone. The reaction was heated at 115° C. for 1 hour and 60° C. for 1.5 hours. It was then poured onto ice, stirred for 45 minutes and the solid filtered and washed with water. The solid was suspended in acetone, stirred for 20 minutes, filtered, washed with petroleum ether, and dried to give 12.3 grams (43%) of white solid 6-(4-bromobutyryl)-benzoxazolone NMR (d, DMSO-d$_6$): 1.77 quin, 2H), 3.00 (t, 2H), 3.45 (t, 2H), 7.0–7.8 (m, 3H).

B. To a 100 ml three-necked round-bottomed flask equipped with dropping funnel, thermometer, and nitrogen inlet were added 10 grams (0.035 mol) 6-(4-bromobutyryl)-benzoxazolone and 26.08 ml (0.35 mol) trifluoroscetic acid. To the stirring suspension was added dropwise 12.93 ml (0.080 mol) triethylsilane, and the reaction stirred at room temperature for 16 hours. The reaction was then poured into water, and the resulting white solid filtered and washed with water. It was then suspended in isopropyl ether, stirred, and filtered to afford white solid 6-(4-trifluoroacetoxybutyl)-benzoxazolone, m.p. 100°–103° C., 10.47 grams (98.7%).

C. To a 250 ml round-bottomed flask equipped with nitrogen inlet were added 5.0 grams (0.0164 mol) 6-(trifluoroacetoxybutyl)-benzoxazolone, 100 ml methanol, and 1 gram sodium carbonate. The reaction was stirred at room temperature for 1 hour, evaporated, and the residue taken up in methylene chloride/methanol, washed with aqueous HCl, dried over sodium sulfate, and evaporated to white solid 6-(4-chlorobutyl)-benzoxazolone, m.p. 130°–133° C., 2.57 grams (75.7%).

E. To a 100 ml round-bottom flask equipped with condenser and nitrogen inlet were added 0.658 grams (3.10 mmol) of 6-(4-chlorobutyl)-benzoxazolone, 0.7 grams (3.10 mmol) of N-(1-naphthyl)piperazine, 0.328 grams sodium carbonate, 2 mg sodium iodide, and 50 ml isopropanol. The reaction was refluxed for 3 days, evaporated, taken up in methylene chloride, washed with water, dried over sodium sulfate, and evaporated. The residue was chromatographed on silica gel using ethyl acetate as eluent, and the product dissolved in acetone, precipitated with ethereal HCl, and the white solid filtered, washed with acetone, and dried to afford 6.76 grams (46.0%) of a white solid, m.p. 231°–233° C.

EXAMPLE 11

6-(2-(4-(3-(N-(3-Trifluoromethyl)phenyl)indazolyl)-piperazinyl)ethyl)benzoxazolone To a 125 ml round-bottomed flask equipped with condenser were added 1.0 gram (2.89 mmol) of N-(3-trifluoromethylphenyl)indazolyl)piperazine, 0.70 grams (2.89 mol) of 6-(2-bromoethyl)benzoxazolone, 0.31 grams (2.89 mmol) of sodium carbonate, and 50 ml of methyl isobutyl ketone, and the mixture refluxed 18 hours. The reaction was cooled and partitioned between ethyl acetate and water. The ethyl acetate layer was isolated, washed with water and saturated aqueous sodium chloride solution, dried over sodium sulfate, and evaporated to an oil. The oil was chromatographed on silica gel using ethyl acetate/methylene chloride as eluent, and the product fractions collection and dissolved in ether, precipitated with hydrochloride gas, and the solid collected to give the hydrochloride salt of the title compound, m.p. 280°–282° C., 0.75 grams (47%).

EXAMPLE 12

5-(2-(4-(1-Naphthyl)piperazinyl)ethyl)oxindole

A. To a 250 ml round-bottomed flask equipped with condenser and nitrogen inlet were added 30.7 grams (230 mmol) aluminum chloride, 150 ml carbon disulfide, and 3.8 ml (48 mmol) chloroacetyl chloride. To the stirring mixture was added 5.0 grams (37 mmol) of oxindole portionwise over 15 minutes. The reaction was stirred a further 10 minutes, then refluxed 2 hours. The reaction was cooled, added to ice, stirred thoroughly, and the beige precipitate filtered, washed with water, and dried to afford 7.67 grams (97%) of 5-chloroacetyl-oxindole. NMR (d, DMSO-d$_6$): 3.40 (s, 2H), 5.05 (s, 2H), 6.8–7.9 (m, 3H).

B. To a 100 ml round-bottomed flask equipped with condenser and nitrogen inlet were added 5.0 grams (23.9 mmol) of 5-chloroacetyl oxindole and 18.5 ml triflouroacetic acid. To the stirring solution was added 8.77 ml (54.9 mmol) of triethylsilane while cooling to prevent exotherm, and the reaction stirred 16 hours at room temperature. The reaction was then poured into ice water, stirred and the beige solid filtered, washed with water and hexane, and dried to give 5-(2-chloroethyl)oxindole, m.p. 168°–170° C., 3.0 grams (64%).

C. To a 50 ml round bottomed flask equipped with condenser and nitrogen inlet were added 370 mg (1.69 mmol) 5-(2-chloroethyl)oxindole, 400 mg (1.69 mmol) N-(1-naphthyl)piperazine hydrochloride, 200 mg (1.69 mmol) sodium carbonate, 2 mg sodium iodide, and 50 ml methylisobutylketone. The reaction was refluxed 24 hours, cooled, and evaporated. The residue was taken up in ethyl acetate, washed with water and brine, dried over sodium sulfate, and evaporated. The residue was chromatographed on silica gel with ethyl acetate, and the product fractions collected and evaporated to give a foam. The foam was dissolved in ether, treated with hydrochloric acid gas, and the precipitate collected, washed with ether, and dried to afford a white solid, m.p. 303°–305° C., 603 mg (84%).

EXAMPLE 13

6-(2-(4-(4-(2-,1,3-Benzothiadiazolyl)piperazinyl) ethyl)-benzoxazolone

A. To a 125 ml round-bottomed flask equipped with condenser and nitrogen inlet were added 2.0 grams (13.2 mmol) 4-amino-2,1,3-benzothiadiazole, 2.54 grams (13.2 mmol) mechlorethamine hydrochloride, 4.19 grams (39.6 mmol) sodium carbonate, 2 mg sodium iodide, and 50 ml ethanol. The reaction was refluxed 2 days, cooled, and evaporated. The residue was taken up in methylene chloride, washed in water, dried over sodium sulfate, and evaporated. The residue was chromatographed on silica gel using ethyl acetate/methanol as eluent, and the product fractions collected and evaporated to an oil of 4-(2,1,3-benzothiadiazolyl)-N-methylpiperazine, 628 mg (20%). NMR (d, CDCl$_3$): 2.5 (s, 3H), 2.8 (m, 4H), 3.6 (m, 4H), 6.8 (m, 1H), 7.5 (m, 2H).

B. To a 25 ml round-bottomed flask equipped with condenser and nitrogen inlet were added 620 mg (2.64 mmol) of 4-(2,1,3-benzothiadiazolyl)-N-methylpiperazine, 0.224 ml (2.64 mmol) vinyl chloroformate, and 15 ml dichloroethane. The reaction was refluxed 16 hours, cooled, and evaporated. The residue was chromatographed on silica gel using methylene chloride/ethyl acetate as eluent, and the product fractions collected to give yellow solid 4-(2,1,3-benzothiadiazolyl)-N-vinyloxycarbonylpiperazine, 530 mg (69%). NMR (d, CDCl$_3$): 3.6 (m, 4H), 3.8 (m, 4H). 4.4–5.0 (m, 2H), 6.6–7.6 (m, 4H).

C. To a 50 ml round-bottomed flask equipped with condenser and nitrogen inlet were added 530 mg (1.83 mmol) 4-(2,1,3-benzothiadiazolyl)-N-vinyloxycarbonylpiperazine and 25 ml ethanol, and the suspension saturated with hydrochloric acid gas. The reaction was refluxed 2.75 hours, cooled and evaporated. The residue was triturated with acetone to give a yellow solid N-(2,1,3-benzothiadiazolyl)-piperazine, m.p. 240°–244° C., 365 mg (62%).

D. To a 125 ml round-bottomed flask equipped with condenser and nitrogen inlet were added 365 mg (1.13 mmol) N-(2,1,3-benzothiadiazolyl)-piperazine, 275 mg (1.13 mmol) 6-(2-bromoethyl)benzoxazolone, 359 mg (3.39 mmol) sodium carbonate, 2 mg sodium iodide and 40 ml ethanol. The reaction was heated at reflux for 2 days, cooled and evaporated. The residue was taken up in methylene chloride, washed with water, dried over sodium sulfate, and evaporated. The residue was chromatographed on silica gel using ethyl acetate/methanol as eluent and the product fractions collected, dissolved in methylene chloride/methanol, precipitated by addition of and ethereal solution of HCl, and the solid filtered, washed with ether, and dried to give 228 mg (45%), m.p. 166°–170° C.

EXAMPLE 14

6-(2-(4-(1-Naphthyl)-piperazinyl)ethyl) benzothiazolone

To a 100 ml round-bottomed flask with condenser and nitrogen inlet were added 1.0 gram (3.88 mmol) of 6-(2-bromoethyl)benzothiazolone, 822 mg (3.88 mmol) N-(1-naphthyl)piperazine, 410 mg (3.88 mmol) sodium carbonate, and 50 ml methylisobutlyketone. The reaction was refluxed for 24 hours, cooled, and evaporated. The residue was taken up in ethyl acetate, wawshed with water and brine, dried over sodium sulfate, and evaporated. The resulting solid was treated with hot ethyl acetate to afford a white solid, m.p. 198°–220° C., 540 mg (36%).

EXAMPLE 15

6-(2-(4-(3-benzoisothiazolyl)piperazinyl)ethyl) benzoxazolone

To a 125 ml round-bottomed flask equipped with condenser were added 4.82 grams (0.022 mol) of N-(3-benzoisothiazolyl)piperazine (prepared according to the procedure given in U.S. Pat. No. 4,411,901), 5.32 grams (0.022 mol) of 6-(2-bromo)ethylbenzoxazolone, 2.33 grams (0.022 mol) of sodium carbonate, and 50 ml of methyl isobutyl ketone. The mixture was refluxed for 18 hours. The reaction was cooled and partitioned between ethyl acetate and water. The ethyl acetate layer was isolated, washed with water and saturated aqueous sodium chloride solution dried over sodium sulfate, and evaporated to an oil. The oil was chromatographed on silica gel using ethyl acetate as eluent, and the product fractions collected and triturated with methylene chloride/isopropyl ether to give a white solid, 1 m.p. 185°–187° C. NMR (CDCl$_3$): 1.7 (bs, 1 H), 2.8 (m, 8H), 3.6 (m, 4H), 6.9–8.0 (m, 7H).

EXAMPLE 16

5-(2-(4-(1,2-benzisothiazol-3-yl)-piperazinyl)ethyl) oxindole

To a 125 ml round-bottom flask equipped with nitrogen inlet and condenser were added 0.62 grams (3.20 mmol) 5-(2-chloroethyl)-oxindole, 0.70 grams (3.20 mmol) sodium carbonate, 2 mg sodium iodide, and 30 ml methylisobutyl ketone. The reaction was refluxed 40 hours, cooled, filtered, and evaporated. The residue was chromatographed on silica gel, eluting the byproducts with ethyl acetate (1 1) and the product with 4% methanol in ethyl acetate (1.5 1). The product fractions ($R_f$=0.2 in 5% methanol in ethyl acetate) were evaporated, taken up in methylene chloride, and precipitated by addition of ether saturated with HCl; the solid was filtered and washed with ether, dried, and washed with acetone. The latter was done by slurrying the solid acetone and filtering. The title compound was obtained as a high melting, non-hygroscopic solid product, m.p. 288°–288.5° C., 0.78 (59%).

In a manner analogous to that for preparing 5-(2-(4-(1,2-benzisothiazol-3-yl)piperazinyl)ethyl)-oxindole, the following compounds were made:

5-(2-(4-(1,2-benzisothiazol-3-yl)piperazinyl)ethyl)-1-ethyloxindole hydrochloride, 25%, m.p. 278°–279° C.;

5-(2-(4-(1,2-benzisothiazol-3-yl)piperazinyl)ethyl)-1-methyloxindolehydrochloride hemihydrate, 42%, m.p. 283°–285° C.; MS(%): 392(1), 232(100), 177(31); Anal. for $C_{22}H_{24}N_4OS \cdot HCl \cdot _{1/2}H_2O$: C 60.33, H 5.98, N 12.79. Found: C 60.37, H 5.84, N 12.77;

5-(2-(4-(1,2-benzisothiazol-3-yl)piperazinyl)ethyl)-1-(3-chlorophenyl)oxindole hydrochloride hydrate, 8%, m.p. 221°–223° C.; MS(%): 488(1), 256(4), 232(100), 177 (15); Anal. for $C_{27}H_{25}ClN_4OS \cdot HCl \cdot H_2O$: C 59.67, H 5.19, N 10.31. Found: C 59.95, H 5.01, N 10.14;

5-(2-(4-(1,2-benzisothiazol-3-yl)piperazinyl)ethyl)-3,3-dimethyloxindole hydrochloride hemihydrate, 40%, m.p. 289°–291° C.; MS(%): 406(1), 232(100), 177(42); Anal. for $C_{23}H_{26}N_4OS \cdot HCl \cdot _{1/2}H_2O$: C 61.11, H 6.24, 12.39. Found: C 61.44, H 6.22, N 12.01;

5-(2-(4-(1,2-benzisothiazol-3-yl)piperazinyl)ethyl)-1,3-dimethyloxindole, 76%, m.p. 256° C.;

5'-(2-(4-(1,2-benzisothiazol-3-yl)piperazinyl)ethyl)-spiro [cyclopentane-1,3'-indoline-]-2'-one hydrochloride hemihydrate, 50%, m.p. 291°–293° C. (dec.); MS(%): 432 (1) 232(100), 200(11), 177(36); Anal. for $C_{25}H_{28}N_4OS \cdot HCl \cdot _{1/2}H_2O$: C 62.81, H 6.33, N 11.72. Found: C 63.01, H. 6.32, N 11.34;

5-(2-(4-(1,2-benzisothiazol-3-yl)piperazinyl)ethyl)-1,3,3-trimethyloxindole hydrochloride hemihydrate, 63%, m.p. 225°–257° C.; MS(%): 420(1), 232(100), 177(37); Anal. for $C_{24}H_{28}N_4OS \cdot HCl \cdot _{1/2}H_2O$: C 61.85, H 6.49, N 12.02. Found: C 61.97, H 6.34, N 11.93;

5-(2-(4-(1,2-benzisothiazol-3-yl)piperazinyl)ether)-6-fluorooxindole hydrochloride hydrate, 18%, m.p. 291°–293°

C.; MS(%): 396(1), 232(100), 177(53); Anal. for $C_{21}H_{21}H_4FOS \cdot HCl_{1/2}H_2O$: C 55.93, H 5.36, N 12.42. Found: C 56.39, H 5.30, N 12.19;

5-(2-(4-(1,2-benzisothiazol-3-yl)piperazinyl)ethyl)-7-fluorooxindole hydrochloride, 9%, m.p. 253° C.;

5-(2-(4-(1,2-benzisothiazol-3-yl)piperazinyl)ethyl)-6-chlorooxindole hydrochloride, 20%, m.p.>300° C.; MS(%): 488(1), 256(4), 232(100), 177(15); Analysis for $C_{21}H_{21}ClN_4OS \cdot HCl_{1/2}H_2O$: C 52.50, H 4.71, N 11.39. Found: C 52.83, H 4.93, N 11.42;

5-(2-(4-(1,2-benzisothiazol-3-yl)piperazinyl)ethyl)-6-fluoro-3,3-dimethyloxindole hydrochloride, 35%, m.p. 284°–286° C.; Anal. for $C_{23}H_{25}FN_4OS \cdot HCl \cdot H_2O$: C 57.67, H 5.89, N 11.70. Found: C 58.03, H 5.79, N 11.77;

5-(2-(4-(1,2-benzisothiazol-3-yl)piperazinyl)butyl) oxindole hemihydrate, 26%, m.p. 131°–135° C.; MS(%): 406(2), 270(8), 243(65), 232(23), 177(45), 163(100); Anal. for $C_{23}H_{26}N_4OS_{1/2}H_2O$: C 66.48, H 6.55, N 13.48. Found: C 66.83, H 6.30, N 13.08;

5-(2-(4-(1,2-benzisothiazol-3-yl)piperazinyl)butyl)-7-fluorooxindole hydrate, 7%, m.p. 126°–129° C.; MS(%): 424(3); Anal. for $C_{23}H_{25}FN_4OS \cdot H_2O$: C 57.67, H 5.89, N 11.70. Found: C 57.96, H 5.62, N 11.47;

5-(2-(4-(1,2-benzisothiazol-3yl)piperazinyl)butyl)-1-ethyloxindole hemihydrate, 25%, m.p. 126°–128° C.; MS(%): 434(2), 298(10), 271(55), 232(34), 177(53), 163 (100); Anal. for $C_{25}H_{30}N_4OS_{1/2}H_2O$: C 67.69, H 7.04, N 12.63. Found: C 67.94, H 6.73, N 12.21;

5-(2-(4-(naphthalen-1-yl)piperazinyl)ethyl)-1-ethyloxindole hydrochloride hydrate, 21%, m.p.>300° C.; MS(%): 399(1), 225(96), 182(30), 70(100); Anal. for $C_{26}H_{29}N_3O \cdot HCl \cdot H_2O$: C 68.78, H 7.10, N 9.26. Found: C 69.09, H 6.72, N 9.20;

5-(2-(4-(naphthalen-1-yl)piperazinyl)ethyl)-6-fluorooxindole hydrochloride, 23%, m.p. 289°–291° C.; MS(%): 389(1), 232(3), 225(100), 182(32), 70(84); Anal. for $C_{24}H_{24}FN_3O \cdot HCl_{1/2}CH_2Cl_2$; C 62.82, H 5.60, N 8.97. Found: C 62.42, H 5.82, N 8.77;

5-(2-(4-(naphthalen-1yl)piperazinyl)ethyl)-7-fluorooxindole hydrochloride, 22%, m.p. 308° C.(dec.); MS(%): 389(1), 225(100); Anal. for $C_{24}H_{24}FN_3O \cdot HCl \cdot CH_2Cl_2$; C 58.78, H 5.93, N 8.23. Found: C 58.82, H 5.80, N 8.27;

EXAMPLE 17

6-(4-(2-(3-Benzisothiazolyl)piperazinyl)ethyl) phenyl)benzothiazolone

To a 100 ml round-bottomed flask equipped with condenser and nitrogen in let were added 1.03 grams (4 mmol) 6-(2-bromoethyl)-benzothiazolone, 0.88 grams (4 mmol) N-benzisothiazolylpiperazine, 0.84 grams (8 mmol) sodium carbonate, 2 mg sodium iodide, and 40 ml methylisobutyl ketone. The reaction was refluxed 36 hours, cooled, filtered, and the filtrate evaporated. The residue was chromatographed on silica gel using ethyl acetate as eluent to afford an oil, which was taken up in methylene chloride and precipitated by addition of ether saturated with HCl. The solid was filtered, washed with ether, dried briefly, washed with a minimal amount of acetone and dried to afford a white solid, m.p. 288°–290° C., 1.44 grams (76.7%).

EXAMPLE A

A. Following the general procedure for the preparation of 5-(chloroacetyl)oxindole in Example 12A, the following intermediates were prepared from the appropriate oxindoles:

5-(chloroacetyl)-1-ethyl-oxindole (81%, m.p. 157°–159° C., NMR(CDCl$_3$); 1.30(t,3H), 3.60(s,2H), 3.85(q,2H), 4.70 (s,2H), 6.85–8.15(m,2H);

5-(chloroacetyl)-1-methyloxindole($C_{11}H_{10}ClNO_2$, 92%, m.p. 201°–202° C.;

1(3-chlorophenyl)-5(chloroacetyl)oxindole, 98% m.p. 143°–145° C., NMR(DMSO-d$_6$): 3.85(br s,2H), 5.10(s,2H), 6.8(d,1H), 7.4–7.6(m,4H), 7.9 (s+d,2H); MS(%): 319(17, 270(100), 179(46), 178(38);

1,3-dimethyl-5-(chloroacetyl)oxindole, 97% m.p. 206°–207° C.

5-(chloroacetyl)-spirocyclopentane[1,3']-indol2'one, 99%, m.p. 203°–204° C.(dec.); NMR(DMSO-d$_6$): 2.0(brs, 8H), 4.95(s,2H), 6.9(d,1H), 7.8(d+s,2H), 10.6(brs, 1H);

5-(chloroacetyl)-1,3,3-trimethyloxindole, 82%, m.p. 182°–185° C., NMR(CDCl$_3$): 1.45(s,6H), 3.25(s,3H), 4.65 (s,2H), 6.9(d,1H), 7.9(s,1H), 8.0(d,1H);

6-fluoro-5-(chloroacetyl)oxindole, 96%, m.p. 178°–180° C.; NMR(DMSO-d$_6$): 3.5(s,2H), 4.8(d,2H), 6.7–7.2(m,2H), 7.8(d,1H);

7-fluoro5-(chloroacetyl)oxindole, 91%, m.p. 194°–196° C., NMR(DMSO-d$_6$): 3.68(s,2H), 5.13(s,2H) 7.65–7.9(dd, 2H);

6-chloro-5-(chloroacetyl)oxindole, 99%, m.p. 206°–207° C.;

5-(chloroacetyl)-3,3-dimethyl-6-fluorooxindole, 89%, m.p. 185°–188° C.;

5-(y-chlorobutyryl)oxindole, 84%, oil, MS(%): 239, 237 (55);

1-ethyl-5-(y-chlorobutyryl)oxindole, 99%, oil, NMR (CDCl$_3$): 1.2(t,3H), 1.5–2.7(m,5H), 3.0–3.2(m,2H), 3.5–4.0 (m,3H), 6.8–7.0(d,1H), 7.9(s,1H), 7.95(d,1H), and 5-(y-chlorobutyryl)-7-fluorooxindole, 53%, m.p. 156°–160° C.

EXAMPLE B

By the same procedure as that used to prepare 5-(2-chlorethyl)oxindole in Example 12B, the following were prepared:

5-(2-chloroethyl)-1-ethyloxindole, 93%, m.p. 120°–122° C.; NMR (CDCl$_3$): 1.30(t,2H), 3.55(s,2H), 3.65–4.0(m,4H), 6.8–7.3(m,3H);

5-(2-chloroethyl)-1-methyloxindole, 99%, m.p. 127°–130° C.; NMR (CDCl$_3$): 3.1(t,2H), 3.2(s,2H), 3.5(s, 2H), 3.75(t,2H), 6.8(d,1H), 7.15(s,1H), 7.3(d,1H);

5-(2-chloroethyl)-1-(3-chlorophenyl)oxindole, 83%, m.p. 75°–76° C.;

5-(2-chloroethyl)-1,3-dimethyloxindole, 58%, m.p. 73°–75° C., NMR CDCl$_3$): 1.45–1.55(d,3H), 3.03–3.2(t, 2H), 3.25(s,3H), 3.30–3.60(q,1H), 3.65–3.90(t,2H), 6.85–6.90(d,1H), 7.15(s,1H), 7.15–7.30(d,1H);

5'-(2-chloroethyl)-spiro[cyclopentane-1,3'-indoline]-2'-one, 92%, m.p. 140°–142° C.; NMR(DMSO-d$_6$): 2.8(brs, 8H), 2.90(t,2H), 3.7(t,2H), 6.6–7.1(m,3H), 10.2(brs,1H);

5-(2-chloroethyl)-,3,3-trimethyloxindole, 83%, oil;

5-(2-chloroethyl)-6-fluorooxindole 62%, m.p. 188°–190° C.; NMR(DMSO-ds) 3.05(t,2H), 3.5(2,2H), 3.85(t,2H), 6.6–7.3(m,2H);

5-(2-chloroethyl)-7-fluorooxindole, 79%, m.p. 176°–179° C.; MS(%); 213(50), 180(20), 164(100), 136(76);

5-(2-chloroethyl)-6-chlorooxindole, 94%, m.p. 210°–211° C.;

5-(2-chloroethyl)-3,3-dimethyl-6-fluorooxindole ($C_{12}H_{13}ClFNO$, 84%, m.p. 195°–196° C., NMR(DMSO-d$_6$): 1.3(s,6H), 3.05(t,2H), 3.7(t,2H), 6.65(d,1H), 7.1(d,1H), 10.1(br s,1H);

5-(4-chlorobutyl)oxindole, 40%, oil, NMR(CDCl$_3$): 1.6–2.0(m,4H), 2.6(m,2H), 3.6(m,4H), 6.8–7.15(m,3H), 9.05(br s,1H);

5-(4-chlorobutyl)-ethyloxindole, 48%, oil, NMR(CDCl$_3$): 1.25(t,3H), 1.5–1.95(m,4H), 2.6(m,2H), 3.5(s,2H), 3.55(t, 2H), 3.75(q,2H), 6.7–7.2(m,3H); and 5-(4-chlorobutyl)-7-fluorooxindole, 71%, m.p. 168°–173° C.

What is claimed is:

1. A method for treating a psychiatric condition or disorder selected from dementia, dementia of the Alzheimer's type, bipolar disorders, mood disorder with depressive features, mood disorder with major depressive-like episode, mood disorder with manic features, mood disorder with mixed features, substance-induced mood disorder and mood disorder not otherwise specified (NOS), panic disorder without agoraphobia, panic disorder with agoraphobia, agoraphobia without history of panic disorder, social phobia, postraumatic stress disorder, acute stress disorder, substance-induced anxiety disorder and anxiety disorder not otherwise specified (NOS), dyskinesias and behavioral manifestations of mental retardation, conduct disorder and autistic disorder in a mammal, including a human, comprising administering to said mammal a pharmaceutically effective amount of a compound of the formula

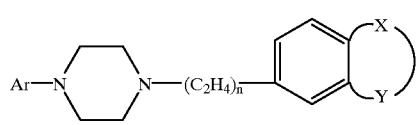

(I)

or a pharmaceutically acceptable acid addition salt thereof, wherein

Ar is benzoisothiazolyl or an oxide or dioxide thereof each optionally substituted by one fluoro, chloro, trifluoromethyl, methoxy, cyano, nitro or naphthyl optionally substituted by fluoro, chloro, trifluoromethyl, methoxy, cyano or nitro; quinolyl; 6-hydroxy-8-quinolyl; isoquinolyl; quinazolyl; benzothiazolyl; benzothiadiazolyl; benzotriazolyl; benzoxazolyl; benzoxazolonyl; indolyl; indanyl optionally substituted by one or two fluoro, 3-indazolyl optionally substituted by 1-trifluoromethylphenyl; or phthalazinyl;

n is 1 or 2; and

X and Y together with the phenyl to which they are attached form quinolyl; 2-hydroxyquinolyl; benzothiazolyl; 2-aminobenzothiazolyl; benzoisothiazolyl; indazolyl; 2-hydroxyindazolyl; indolyl; spiro; oxindolyl optionally substituted by one to three of (C$_1$–C$_3$)alkyl, or one of chloro, fluoro or phenyl, said phenyl optionally substituted by one chloro or fluoro; benzoxazolyl; 2-aminobenzoxazolyl; benzoxazolonyl; 2-aminobenzoxazolinyl; benzothiazolonyl; bezoimidazolonyl; or benzotriazolyl.

2. A method according to claim 1, wherein said method is for treating dementia.

3. A method according to claim 2, wherein dementia is selected from the group consisting of vascular dementia, dementia due to HIV disease, dementia due to head trauma, dementia due to Parkinson's disease, dementia due to Huntington's disease, dementia due to Pick's disease, dementia due to Creutzfeldt-Jakob disease, substance-induced persisting dementia, dementia due to multiple etiologies and dementia not otherwise specified (NOS).

4. A method according to claim 1, wherein said method is for treating dementia of the Alzheimer's type.

5. A method according to claim 4, wherein dementia of the Alzheimer's type is selected from the group consisting of dementia of the Alzheimer's type with early onset uncomplicated, dementia of the Alzheimer's type with early onset with delusions, dementia of the Alzheimer's type with early onset with depressed mood, dementia of the Alzheimer's type with late onset uncomplicated, dementia of the Alzheimer's type with late onset with delusions and dementia of the Alzheimer's type with late onset with depressed mood.

6. A method according to claim 1, wherein bipolar disorders are selected from the group consisting of bipolar I or II disorder single manic episode, bipolar I or II disorder most recent episode hypomanic, bipolar I or II disorder most recent episode manic, bipolar I or II disorder most recent episode mixed, bipolar I or II disorder most recent episode depressed, cyclothymic disorder and bipolar disorder not otherwise specified (NOS).

7. A method according to claim 6, wherein the current state of bipolar I or II disorder single manic episode, bipolar I or II disorder most recent episode manic, bipolar I or II disorder most recent episode depressed are each characterized as mild, moderate, severe without psychotic features, in partial remission or in full remission.

8. A method according to claim 1, wherein said method is for treating dyskinesias.

9. A method according to claim 8, wherein dyskinesias is selected from drug-induced dyskinesias and neurodegenerative based dyskinesias.

10. A method according to claim 1, wherein said method is for treating behavioral manifestations of mental retardation.

11. A method according to claim 1, wherein mental retardation is selected from the group consisting of mild mental retardation, moderate mental retardation, severe mental retardation, profound mental retardation and mental retardation severity unspecified.

12. A method according to claim 1, wherein said method is for treating behavioral manifestations of conduct disorder.

13. A method according to claim 1, wherein said method is for treating behavioral manifestations of autistic disorder.

14. A method according to claim 1, wherein X and Y together with the phenyl to which they are attached form benzoxazolonyl.

15. A method according to claim 2, wherein Ar is benzoisothiazolyl and n is 1.

16. A method according to claim 1, wherein X and Y together with the phenyl to which they are attached form oxindole optionally substituted by chloro, fluoro or phenyl.

17. A method according to claim 1, wherein Ar is naphthyl and n is 1.

* * * * *